(12) United States Patent
Rosenberg

(10) Patent No.: US 7,691,964 B2
(45) Date of Patent: Apr. 6, 2010

(54) PEPTIDE ANTI-TUMOR AGENT

(75) Inventor: Martin Jay Rosenberg, Brooklyn, NY (US)

(73) Assignee: New York University, New York, NY (US)

( * ) Notice: Subject to any disclaimer, the term of this patent is extended or adjusted under 35 U.S.C. 154(b) by 201 days.

(21) Appl. No.: 11/615,723

(22) Filed: Dec. 22, 2006

(65) Prior Publication Data
US 2007/0123454 A1    May 31, 2007

Related U.S. Application Data

(62) Division of application No. 11/264,684, filed on Oct. 31, 2005, now Pat. No. 7,173,110.

(60) Provisional application No. 60/626,220, filed on Nov. 8, 2004.

(51) Int. Cl.
*A61K 38/12* (2006.01)
*A61K 38/00* (2006.01)
*A61K 51/00* (2006.01)

(52) U.S. Cl. ............................ 530/317; 514/2; 424/1.69

(58) Field of Classification Search .................. 514/12, 514/2; 530/317; 424/1.69
See application file for complete search history.

(56) References Cited

U.S. PATENT DOCUMENTS 4,307,082 A    12/1981    Rosenberg et al.
4,530,784 A    7/1985    Rosenberg

FOREIGN PATENT DOCUMENTS

WO    03/072737    9/2003

OTHER PUBLICATIONS

Guru. Cancer Models-Systems for identifying new drugs are often faulty. Science 278, 1041-2 (Nov. 7, 1997).*
Higgins, P.J et al., "Contact-inhibitory factor induces alterations in the distribution and content of specific cytoskeletal elements in an established line of rat hepatic tumor cells." Int J Cancer, vol. 40, 1987, pp. 792-801, XP002470458.

* cited by examiner

*Primary Examiner*—Maury Audet
(74) *Attorney, Agent, or Firm*—Darby & Darby P.C.

(57) ABSTRACT

Disclosed herein are isolated, purified peptides, biologically active fragments and analogs of the peptides having anti-tumor activity in mammals, pharmaceutical formulations comprising the peptides, fragments and analogs and methods of treating mammals suffering from tumors using such materials.

7 Claims, 12 Drawing Sheets

AXIMA MALDI-TOF MS Spectra of Acetonitrile Fraction

AXIMA MALDI-TOF MS Spectra of 1098 Ion Isotope Series

QSTAR MALDI-TOF-MS Spectra of the Propanol Fraction

QSTAR MALDI-TOF MS/MS Spectra of the 1098 Ion

Annotated QSTAR MALDI-TOF MS/MS Sequence of the 1098 Ion

Annotated Qstar MALDI-TOF MS/MS Sequence of 1108 Ion

SEQUENCE LISTING

<160> NUMBER OF SEQ ID NOS: 7

<210> SEQ ID NO 1
<211> LENGTH: 10
<212> TYPE: PRT
<213> ORGANISM: artificial
<220> FEATURE:
<223> OTHER INFORMATION: synthetic peptide

<400> SEQUENCE: 1

Gly Met Met Cys Val Thr His Cys Asn Gly
1               5                   10

<210> SEQ ID NO 2
<211> LENGTH: 10
<212> TYPE: PRT
<213> ORGANISM: artificial
<220> FEATURE:
<223> OTHER INFORMATION: synthetic peptide

<400> SEQUENCE: 2

Gly Met Met Cys Val Ser His Cys Asn Gly
1               5                   10

<210> SEQ ID NO 3
<211> LENGTH: 10
<212> TYPE: PRT
<213> ORGANISM: artificial
<220> FEATURE:
<223> OTHER INFORMATION: synthetic peptide

<400> SEQUENCE: 3

Cys Met Met Asn Thr Ser Cys Met Val Leu
1               5                   10

<210> SEQ ID NO 4
<211> LENGTH: 10
<212> TYPE: PRT
<213> ORGANISM: artificial
<220> FEATURE:
<223> OTHER INFORMATION: synthetic peptide

<400> SEQUENCE: 4

Cys Met Met Asn Thr Ser Cys Met Val Ile
1               5                   10

<210> SEQ ID NO 5
<211> LENGTH: 10
<212> TYPE: PRT
<213> ORGANISM: artificial
<220> FEATURE:
<223> OTHER INFORMATION: synthetic sequence
<220> FEATURE:
<221> NAME/KEY: MISC_FEATURE
<222> LOCATION: (2)..(3)
<223> OTHER INFORMATION: Xaa is Met(O)

<400> SEQUENCE: 5

Gly Xaa Xaa Cys Val Thr His Cys Asn Gly
1               5                   10

<210> SEQ ID NO 6
<211> LENGTH: 10
<212> TYPE: PRT
<213> ORGANISM: artificial
<220> FEATURE:

```
<223> OTHER INFORMATION: synthetic sequence
<220> FEATURE:
<221> NAME/KEY: DISULFID
<222> LOCATION: (4)..(8)

<400> SEQUENCE: 6

Gly Met Met Cys Val Thr His Cys Asn Gly
1               5                   10

<210> SEQ ID NO 7
<211> LENGTH: 10
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: Xaa is Cys(Trt)
<220> FEATURE:
<221> NAME/KEY: MISC_FEATURE
<222> LOCATION: (6)..(6)
<223> OTHER INFORMATION: Xaa is Thr(tBu)
<220> FEATURE:
<221> NAME/KEY: MISC_FEATURE
<222> LOCATION: (7)..(7)
<223> OTHER INFORMATION: Xaa is His(Trt)
<220> FEATURE:
<221> NAME/KEY: MISC_FEATURE
<222> LOCATION: (8)..(8)
<223> OTHER INFORMATION: Xaa is Cys(Trt)
<220> FEATURE:
<221> NAME/KEY: MISC_FEATURE
<222> LOCATION: (9)..(9)
<223> OTHER INFORMATION: Xaa is Asn(Trt)

<400> SEQUENCE: 7

Gly Met Met Xaa Val Xaa Xaa Xaa Xaa Gly
1               5                   10
```

US 7,691,964 B2

PEPTIDE ANTI-TUMOR AGENT

This application is a divisional of co-pending Ser. No. 11/264,684. The entire disclosure of said application is hereby incorporated by reference it its entirety.

This application claims priority under 35 U.S.C. §119(e) from U.S. Provisional Patent Application Ser. No. 60/626,220, filed Nov. 8, 2004 of which is incorporated by reference in its entirety.

FIELD OF THE INVENTION

This application is directed to isolated peptides having anti-tumor activity in mammals, pharmaceutical formulation comprising the peptides, and methods of use thereof.

BACKGROUND OF THE INVENTION

A Contact Inhibitory Factor (CIF), derived from hamster (FF) and mouse (AM) cell lines has been shown to restore in vitro growth control to malignant melanoma cells, including contact-, serum-, and anchorage-dependent growth. The contact inhibitory effects are neither tissue nor species specific, extending to a broad spectrum of organ derived tumors, including colon, breast, brain, prostate and muscle. CIF also induces, in melanoma cells, the reappearance of pigment differentiation antigens, increases expression of Class I MHC antigens and enhances recognition and destruction of melanoma cells by cytotoxic T cells. CIF also reorganizes the cytoskeleton of melanoma cells in a more normal direction, decreases chemotaxis to laminin and decreases the surface expression of intercellular adhesion molecule 1 (ICAM-1) on melanoma cells.

CIF has been found to be non-toxic in vitro. In vivo it has been found to lead to regression of melanoma in hamsters (100%) and Lewis Lung carcinoma in mice (75%) without toxicity to the surrounding tissues.

Investigation of mechanisms which may contribute to the regression of tumors demonstrated that CIF-mediated reversion of the malignant phenotype is accompanied by several changes in the antigenic profile of the melanoma cells. First, CIF induces the synthesis of vitiligo-related pigment differentiation antigens on mouse and hamster melanoma cells, which had lost these antigens (Lipkin et al., 1985), providing a potential target for immune destruction by both antibody-dependent cellular cytotoxicity and complement-mediated lysis (Norris et al., 1986). Secondly, CIF increases expression of Class I MHC antigens on mouse melanoma cells, with accompanying increase in susceptibility to lysis by cytotoxic (CD8) T lymphocytes. Both changes would make melanoma cells much better targets for the host's immune system.

However, an additional mechanism is suggested by the high vascularity of both melanomas and Lewis lung carcinomas. It is now well established that colonies of tumor cells require ingrowth of new blood vessels from the surrounding host vasculature in order to progress beyond a few mm in size (Folkman, 1985). Melanomas induce angiogenesis by secreting angiogenic molecules such as VEGF and FGF-2. Among melanocytic lesions there is a stepwise increase in vascularity with histologic progression from benign nevus to dysplastic nevus, primary cutaneous malignant melanoma and, finally, metastatic malignant melanoma (Barnhill et al., 1992). In fact, even for thin melanomas (<0.76 mm Breslow thickness), with a 5 year survival rate of 95%, high vessel counts are predictive of metastasis and death (Graham et al., 1994).

U.S. Pat. No. 4,307,082 issued Dec. 22, 1981 discloses a method for the extraction of CIF from media conditioned by the growth of a contact inhibited cell culture. The factor was purified by passage through a phenyl sepharose column. The factor was said to be a non-dialyzable protein or carbohydrate having a molecular weight of greater than 10,000 Daltons, was "mildly hydrophobic" and was stainable with Coomassie brilliant blue.

U.S. Pat. No. 4,530,784 issued Jul. 23, 1985 discloses a method for the large scale extraction of CIF. The protein component of the medium from a contact inhibited cell line was extracted by using a volatile non-denaturing agent and biologically acceptable ionic buffer. It was said that although the CIF obtained was not as pure as that obtained from the '082 patent, the method resulted in a substantially higher quantity and yield.

PCT application No. PCT/US03/05563 filed Feb. 24, 2003, published as WO 03/072,73702 discloses CIF-mediated inhibition of tumor metastasis and angiogenesis.

All of the above described studies used partially purified materials and provided little or no information regarding the physiochemical properties of the CIF molecule.

SUMMARY OF THE INVENTION

The present invention is based on the surprising discovery that a peptide comprising up to ten amino acid residues has anti-tumor activity when administered to mammals in need thereof.

In one aspect, the present invention provides a purified, isolated peptide comprising an amino acid sequence as set forth in SEQ ID NO:1, biologically active fragments and analogs thereof.

In another aspect, the present invention provides a pharmaceutical formulation for treating tumors in mammals comprising a purified, isolated peptide comprising an amino acid sequence as set forth in SEQ ID NO:1, biologically active fragments and analogs thereof, and a pharmaceutically acceptable carrier.

In a further aspect the present invention provides a method for treating a tumor in a mammal comprising administering to a mammal in need of such treatment an amount effective to treat the tumor of a purified, isolated peptide comprising an amino acid sequence as set forth in SEQ ID NO:1, biologically active fragments and analogs thereof, and a pharmaceutically acceptable carrier.

These and other aspects of the present invention will be apparent to those of ordinary skill in the art in light of the present description, claims and drawings.

DETAILED DESCRIPTION OF THE INVENTION

Definitions

Figure 1:
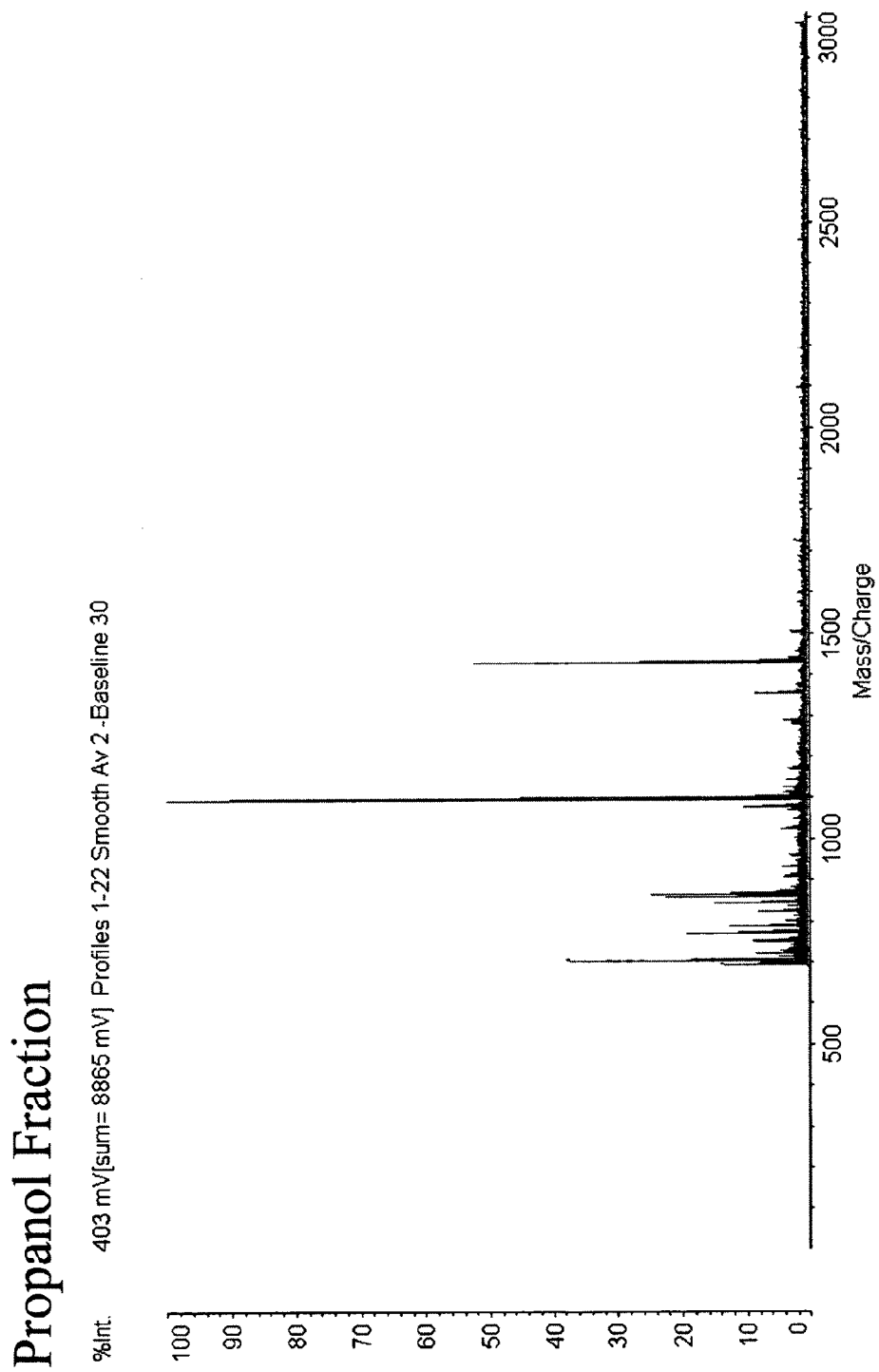
FIG. 1 is a graph showing the AXIMA MALDI-TOF MS Spectra of the Propanol Fraction.
Figure 2:
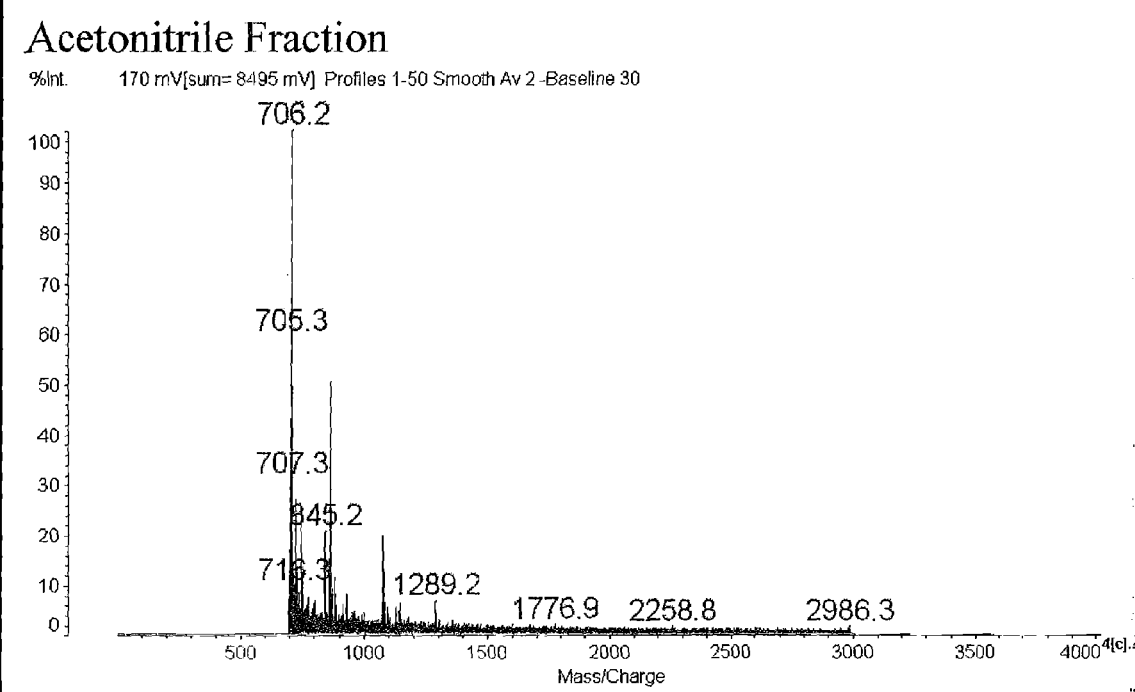
FIG. 2 is a graph showing the AXIMA MALDI-TOF MS Spectra of the Acetonitrile Fraction.
Figure 3:
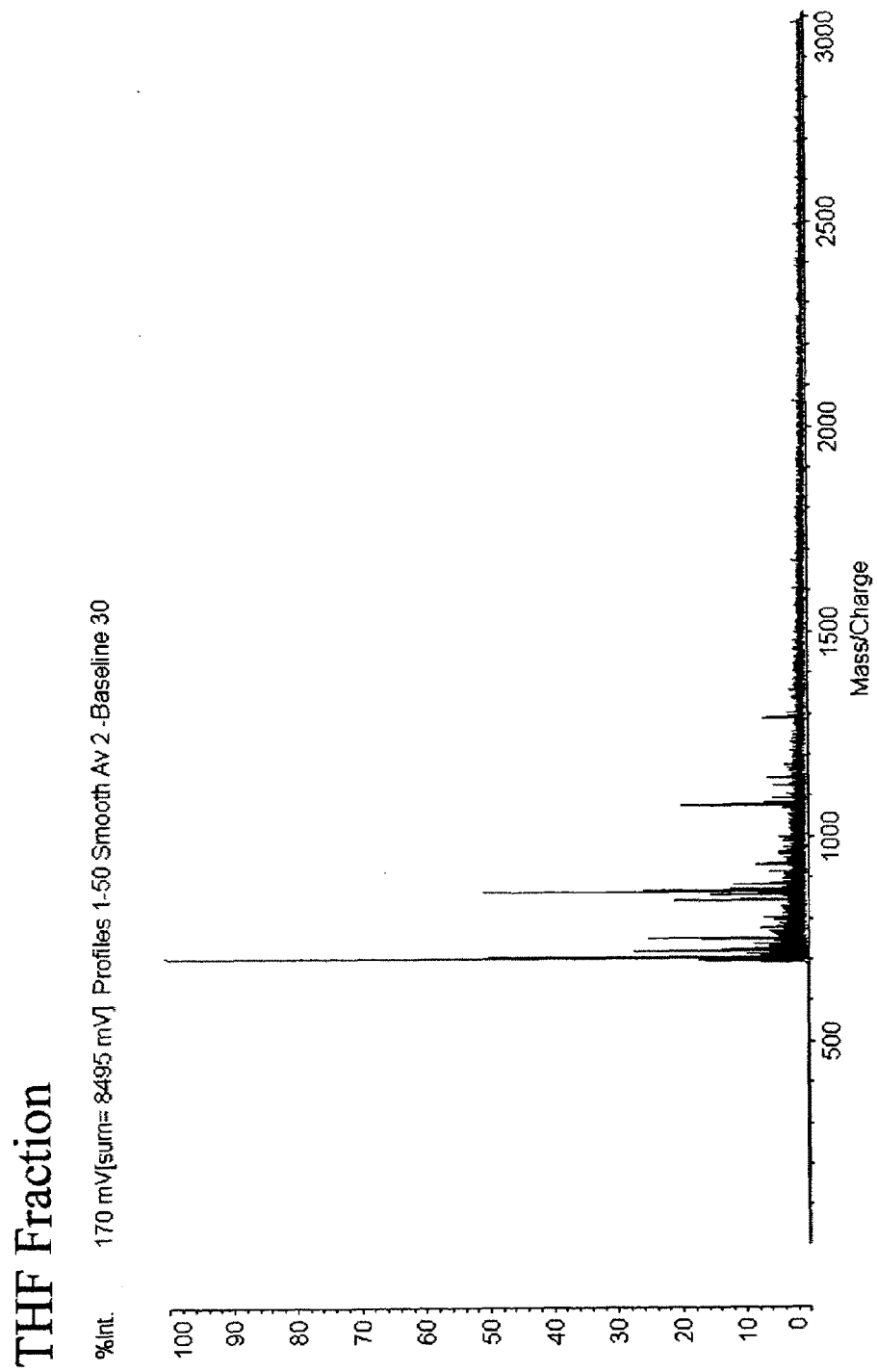
FIG. 3 is a graph showing the AXIMA MALDI-TOF MS Spectra of the THF Fraction
Figure 4:
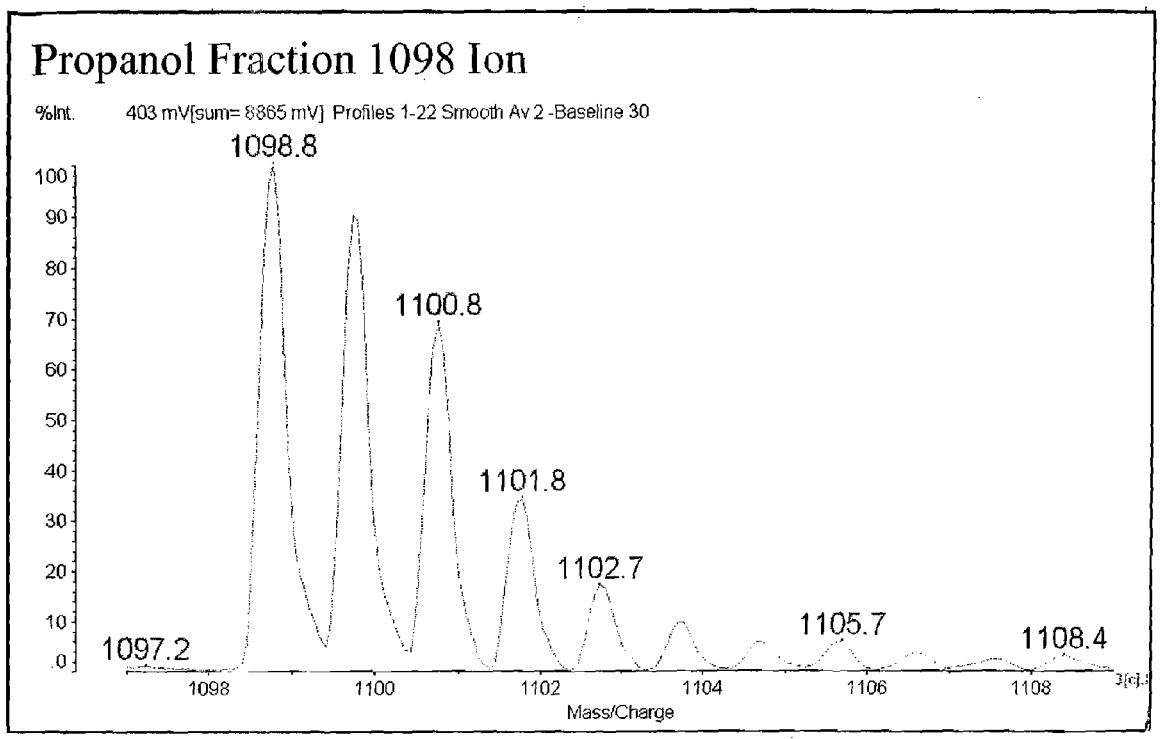
FIG. 4 is a graph showing the AXIMA MALDI-TOF MS Spectra of the 1098 Ion Isotope Series.

The term about or approximately means within an acceptable error range for the particular value as determined by one of ordinary skill in the art, which will depend in part on how the value is measured or determined, i.e., the limitations of the measurement system. For example, about can mean within 1 or more than 1 standard deviations, per the practice in the art. Alternatively, about can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "isolated" means that the referenced material is removed from its native environment, e.g., a cell. Thus, an isolated biological material can be free of some or all cellular components, i.e., components of the cells in which the native material occurs naturally (e.g., cytoplasmic or membrane component). A material shall be deemed isolated if it is present in a cell extract or if it is present in a heterologous cell or cell extract. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified. In terms of cells in culture an isolated protein is present in the tissue culture medium.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including without limitation preparative solid phase chromatography, oligonucleotide hybridization, and triple helix chromatography), ultracentrifugation, and other means. Polypeptides and proteins can be purified by various methods including, without limitation, preparative disc-gel electrophoresis and isoelectric focusing; affinity, HPLC, reversed-phase HPLC, gel filtration or size exclusion, ion exchange and partition chromatography; precipitation and salting-out chromatography; extraction; and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible and contemplated herein. A purified material may contain less than about 50%, preferably less than about 75%, and most preferably less than about 90%, of the cellular components, media, proteins, or other nondesirable components or impurities (as context requires), with which it was originally associated. The term "substantially pure" indicates the highest degree of purity which can be achieved using conventional purification techniques known in the art.

"Anti-tumor" activity is defined herein as any reduction in tumor mass or tumor burden after administration of the peptides or formulations pursuant to the present invention.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Trytophan is Trp or W; Arginine is Arg or R; and Glycine is Gly or G.

As used herein, the term "polypeptide" refers to an amino acid-based polymer, which can be encoded by a nucleic acid or prepared synthetically. Polypeptides can be proteins, protein fragments, chimeric proteins, etc. Generally, the term "protein" refers to a polypeptide expressed endogenously in a cell. An "amino acid sequence" is any chain of two or more amino acids. The term "peptide" is usually used for amino acid-based polymers having fewer than 100 amino acid constituent units, whereas the term "polypeptide" is reserved for polymers having at least 100 such units. Herein, however, "polypeptide" will be the generic term for proteins and peptides as well as polypeptides.

The present invention is based on the unexpected finding that peptides having a molecular weight of about 1034 daltons containing 10 amino acid residues have antitumor activity upon administration to mammals in need thereof. Surprisingly, 2 out of the 10 amino acid residues are adjacent methionines, and 2 out of 10 amino acid residues are cystein. Moreover, in one embodiment the peptide is cyclic, whereas in another embodiment at least one of the methionine residues is oxygenated. In a further embodiment, the peptide contains a cys-cys disulfide bond. The peptides of the present invention may also have combinations of these properties. In a particularly preferred embodiment, the peptide is cyclic, contains at least two oxygenated methionine amino acid residues and a cys-cys disulfide bond. Example 4 below describes the synthesis of two of the peptides of the present invention. Both peptides are cyclic, one has two oxygenated methionine residues and the other has a cys-cys bond. Both are biologically active.

Figure 8:
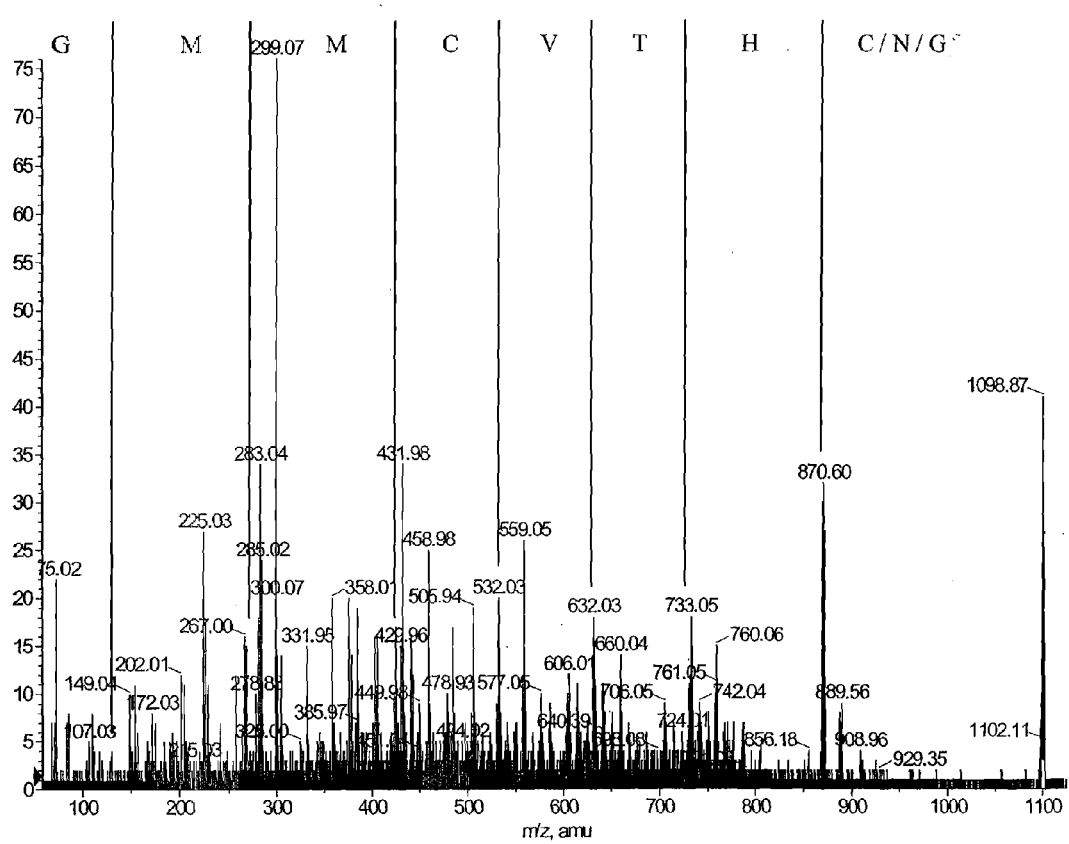
FIG. 8 is the Annotated QSTAR MALDI-TOF MS/MS Sequence of the 1098 Ion.
Figure 10:
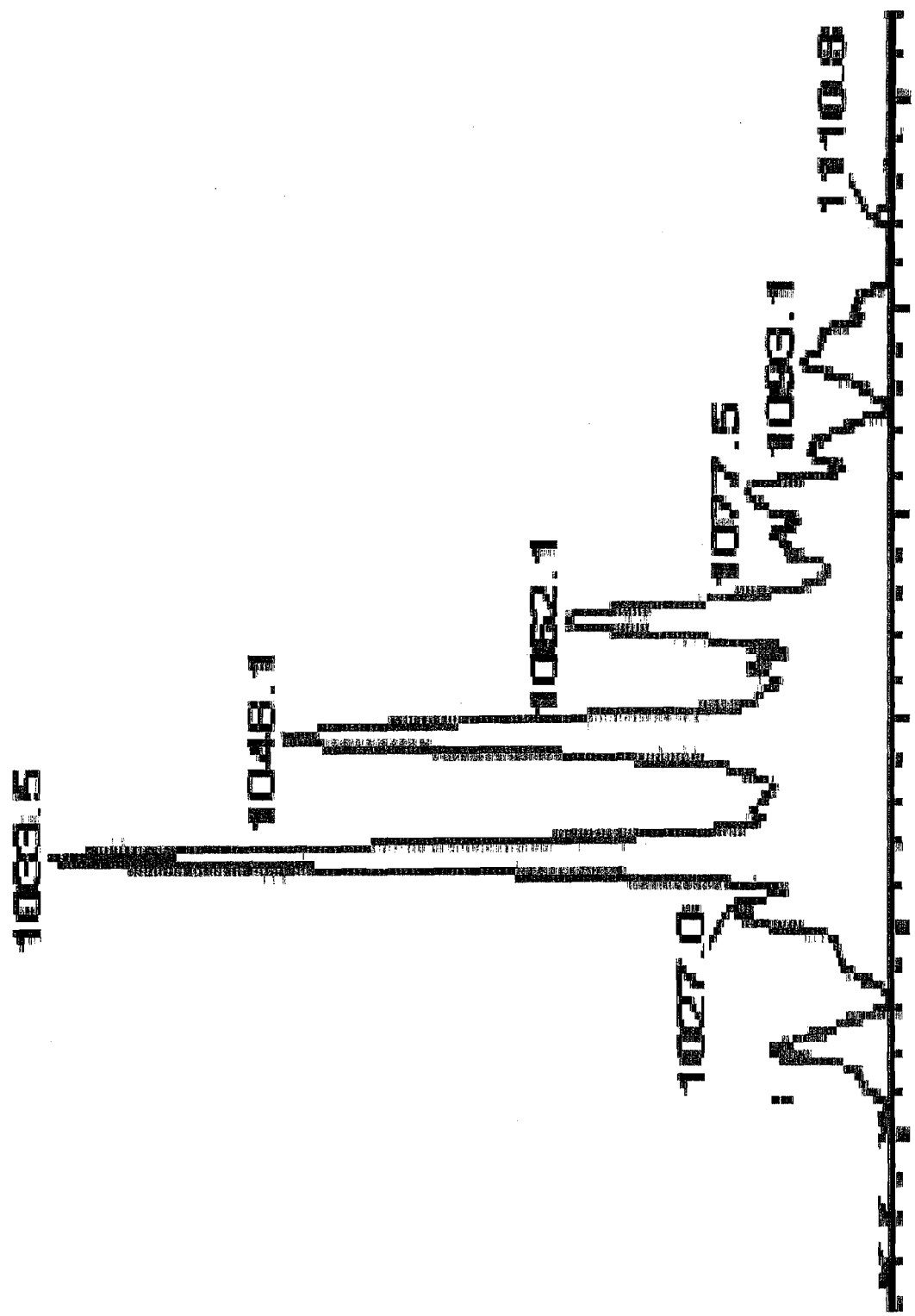
FIG. 10 is a mass spectrogram of the peptide of the present invention isolated from the conditioned medium of amelanotic melanoma cells in culture and purified on an analytical MCX column.
Figure 11:
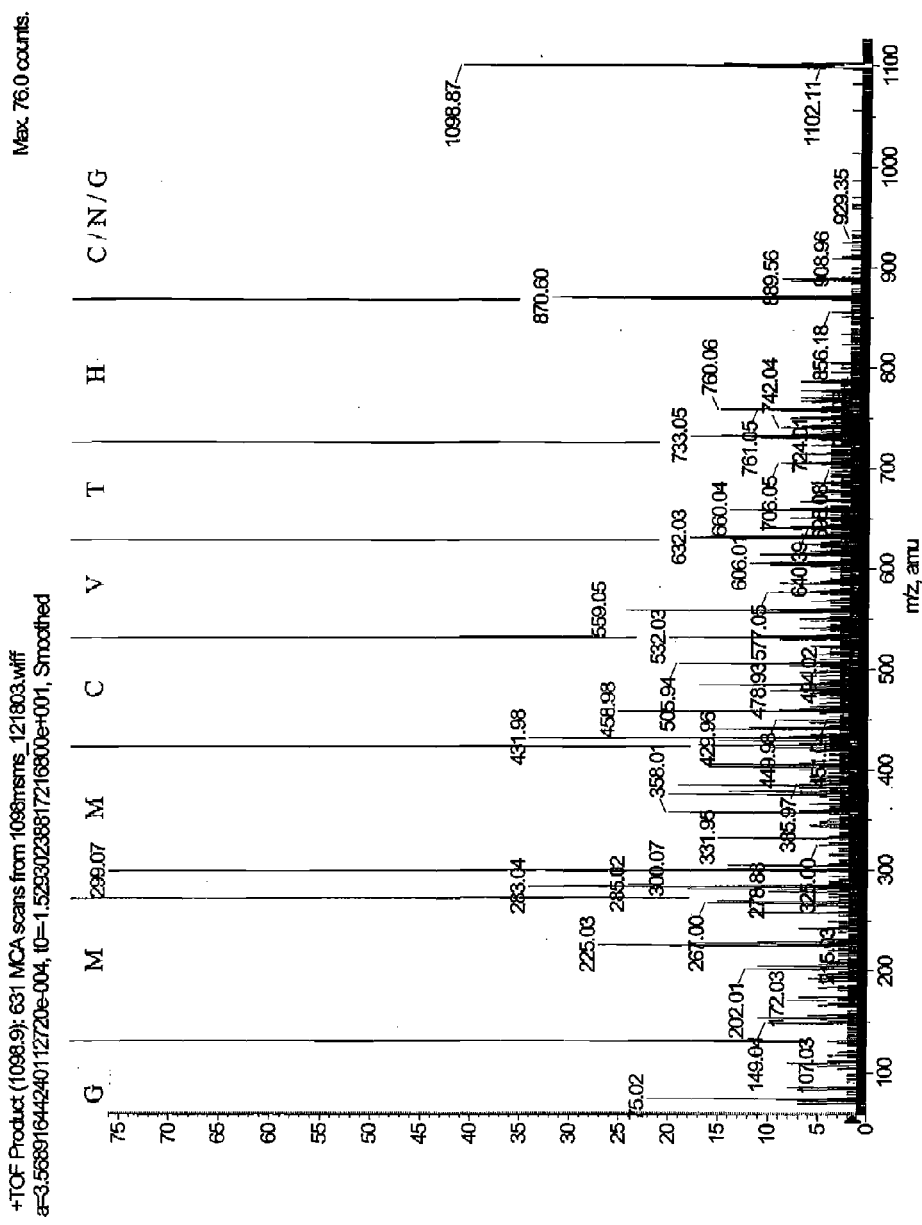
FIG. 11 is mass spectrogram of the peptide of the present invention isolated from the conditioned media of amelanotic melanoma cells in culture and purified on an analytical MCX column.

FIG. 10 shows a mass spectrogram of the peptide of the present invention isolated and purified from the conditioned media of cells in culture as described in Examples 1 and 2 below. The five peaks in FIG. 10 represent five oxidation states from 0 to 4 oxygens. The peptides have 2 adjacent methionine amino acid residues each of which can bind 0, 1 or 2 oxygens. The molecular weight of the unoxygenated species is about 1034 daltons. Each additional oxygen adds about 16 daltons to the molecular weight. The "1098 ion" shown in the mass spectrograms of FIGS. 8, 10 and 11 represents the 1034 peptide plus 4 oxygens (1034+64=1098).

In one embodiment, the peptide of the present invention has the following amino acid sequence: Gly-Met-Met-Cys-Val-Thr-His-Cys-Asn-Gly (SEQ ID NO: 1), and is a linear peptide. Methods to cyclize linear peptides are known to those of ordinary skill in the art and are described in Examples 4 and 6 below. Mammalian cells have the machinery to cyclize linear peptides as evidenced by the fact that when the agent was isolated from the culture medium of cells in culture and purified, it was cyclic. In any event, linear peptides of the invention are useful as precursors to the active cyclic agents.

Figure 9:
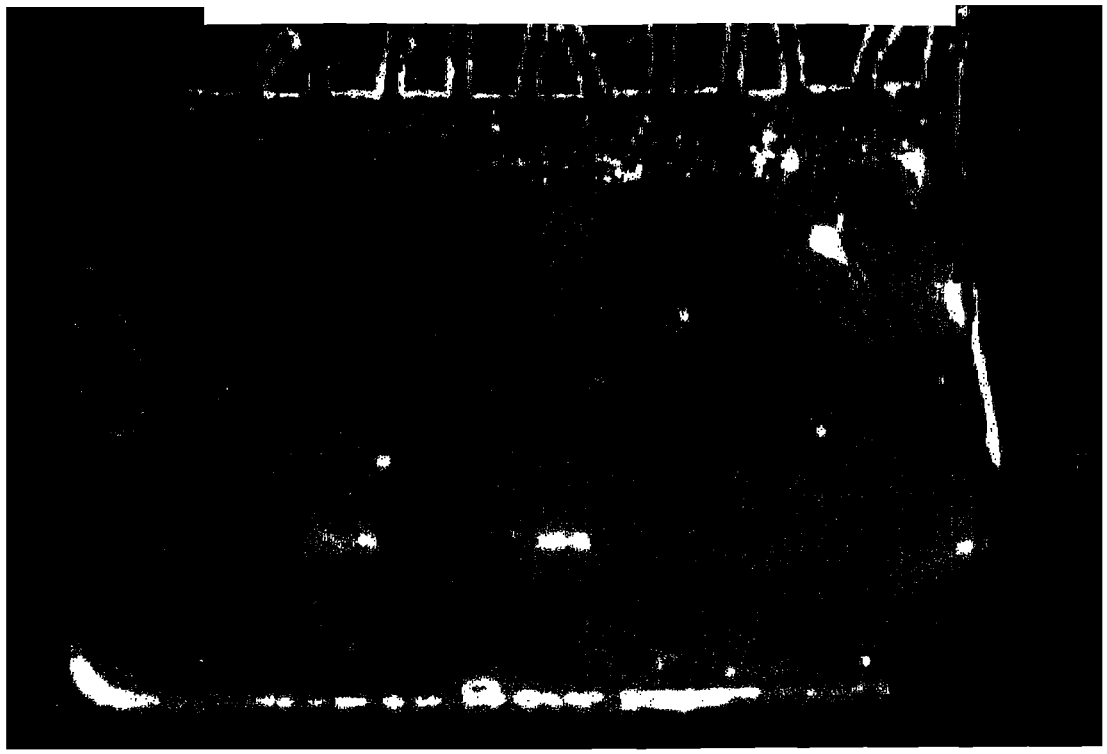
FIG. 9 is a stained 10-20% polyacrylamide gradient gel showing the peptide of the present invention isolated from the conditioned media of cells in culture.

FIG. 9 shows a 10-20% polyacrylamide gradient gel from which the peptide of the present invention was isolated from the conditioned medium of amelanotic melanoma cells in culture before sequence determination. It should be noted that the protein was not stainable with the well known Coomassie brilliant blue or silver staining reagents due to a lack of aromatic amino acid residues. The stain used was SYPRO. SYPRO Ruby dye is a permanent stain comprised of ruthenicum as part of an organic complex that interacts non-covalently with proteins. SYPRO Ruby Protein Gel Stain can be visualized using a wide range of excitation sources commonly used in image analysis systems including a 302 nm UV-B transilluminator, 473 nm second harmonic generation (SHG) laser, 488 nm argon-ion laser, 532 nm yttrium-aluminum-garnet (YAG) laser, xenor arc lamp, blue fluorescent light bulb or blue light-emitting diode (LED). The sensitivity of SYPRO Ruby Protein Gel Stain is superior to colloidal Coomassie Brilliant Blue (CBB) stain or monobromobimane labeling and comparable with the highest sensitivity silver or zinc-imidazole staining procedures available.

The peptides of the present invention can be tested for biologic activity in the bioassay described in Example 4 below. Only cyclic peptides demonstrated activity in this assay. Without wishing to be bound by theory, it is believed that the peptides of the present invention must enter cells to manifest their activity. However, it is possible that upon administration to animals, a linear peptide would be cyclized.

The assay is semi-quantitative. Each day the assay is performed, both a positive and a negative control are included. The positive control is a previously tested sample which yields a constant 4+ result in the assay. It has been found that agents which are active in this assay have anti-tumor activity when administered to mammals.

The peptides of the present invention were discovered during attempts to purify CIF. However, because the cells from which the peptides were isolated were cultured under different conditions and the purification was performed using different techniques and equipment than were employed previously, the relationship between CIF and the peptides of the present invention is currently unknown and may never be elucidated. All that can be currently stated is that the peptides of the present invention share some of the biological activities with CIF. In addition, the peptides of the present invention have been purified to homogeniety and their amino acid sequence determined, whereas CIF was, at best, partially purified and poorly characterized.

The peptide of the present invention isolated from the culture medium conditioned by growth of amelanotic melanoma (AM) cells in culture (hereinafter "conditioned Medium") which were cultivated under serum-free conditions. The cells were "weaned" off serum by slowly reducing the serum concentration as shown in Example 1 below. The peptide was purified by binding to a MCX column using High Performance Liquid Chromatography (HPLC). It was eluted with propanol, a characteristic of highly hydrophobic proteins.

The MCX column is a mixed-mode sorbent. If functions as hydrophobic affinity column and as a cationic exchanger. It contains sulfonic acid derivatives of N-vinylpyrrolidone and divinylbenzene.

The peptides of the present invention include biologically active fragments and analogs of the antitumor agent. "Biologically active fragments" of the peptides of the present invention are those with less than the 10 amino acid residues of the parent compound. Such peptides can be prepared by conventional solid phase synthesis techniques, such as those described in Example 4 below and tested for antitumor activity in the in vitro assay described in Example 5 below. As mentioned above, it has been found that agents which demonstrate activity in this cell based assay have antitumor activity in mammals. Thus, there is a direct correlation.

Examples of analogs are function-conservative variants. "Function-conservative variants" are those in which a given amino acid residue in a protein has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine.

In another example, serine is replaced with threonine. This analog has been isolated from the conditioned medium of cells in culture as described in Example 8 below. Such changes are expected to have little or no effect on the apparent molecular weight or isoelectric point of the protein or polypeptide. Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST OR FASTA algorithms, preferably at least 90%, and which has the same or substantially similar properties or functions as the native or parent protein to which it is compared.

The present invention also provides pharmaceutical formulations comprising the peptides of the present invention, biologically active fragments of the peptides and analogs thereof. The formulations may be administered systemically, e.g., orally and are preferably administered parenterally and most preferably intravenously. Formulations suitable for parenteral, administration may include aqueous and non-aqueous carriers and diluents such as sterile injection solutions, which may contain anti-oxidants, buffers, bacteriostatic agents and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described. The pharmaceutical formulations may also contain pharmaceutically acceptable carriers or diluents.

The phrase "pharmaceutically acceptable" refers to molecular entities and compositions that are generally regarded as safe, e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Nasal aerosol and inhalation formulations of the invention may be prepared by any method in the art. Such formulations may include dosing vehicles, such as saline; preservatives, such as benzyl alcohol; absorption promoters to enhance bioavailability; flurocarbons used in the delivery systems, e.g., nebulizers, etc.; solubilizing agents; dispersing agents; or any combination of any of the foregoing.

The formulations of the present invention may be administered systemically. The term "systemic" as used herein includes parenteral, topical, oral, spray inhalation, rectal, nasal and, buccal administration. The term "parenteral" as used herein includes subcutaneous, intravenous, intramuscular, intra-articular, intra-synovial, intrasternal, intrathecal, intrahepatic, intralesional and intracranial administration. Preferably, the compositions are administered orally, intraperitoneally or intravenously.

In an alternative preferred embodiment, the present invention provides methods for the treatment of tumors in mammals, particularly solid tumors. Examples of solid tumors that can be treated according to the invention include sarcomas and carcinomas such as, but not limited to: fibrosarcoma, myxosarcoma, chondrosarcoma, osteogenic sarcoma, angiosarcoma, endotheliosarcoma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, sweat gland carcinoma, sebaceous gland carcinoma, renal cell carcinoma, hepatoma, bile duct carcinoma, cervical cancer, testicular tumor, lung carcinoma, bladder carcinoma, epithelial carcinoma, melanoma, and retinoblastoma.

The method comprises administering to a mammal in need of such treatment an amount of the peptides of the present invention, including biologically active fragments of the peptides and analogs thereof effective to treat said tumors. This is also known as a therapeutically effective amount of the peptides of the present invention.

The phrase "therapeutically effective amount" is used herein to mean an amount sufficient to reduce by at least about 15 percent, preferably by at least 50 percent, more preferably by at least 90 percent, and most preferably prevent growth and/or metastasis of a tumor and a clinically significant deficit in the activity, function and response of the host. Alternatively, a therapeutically effective amount is sufficient to cause an improvement in a clinically significant condition in the host e.g., a reduction in the tumor burden.

Effective Amounts

As used herein the term "therapeutically effective" or "effective amount" applied to dose or amount refers to that quantity of a compound or pharmaceutical composition that is sufficient to result in a desired activity upon administration to a mammal in need thereof. More specifically, the term "therapeutically effective" refers to that quantity of a compound or pharmaceutical composition that is sufficient to reduce or eliminate a tumor in a mammal. Note that when a combination of active ingredients is administered the effective amount of the combination may or may not include amounts of each ingredient that would have been effective if administered individually.

The optimal therapeutically effective amount may be determined experimentally, taking into consideration the exact mode of administration, the form in which the drug is administered, the indication toward which the administration is directed, the subject involved (e.g., body weight, health, age, sex, etc.), and the preference and experience of the physician or veterinarian in charge. As disclosed herein, for human administration, the peptides of the present invention are administered in suitable form in doses ranging between about 0.1 and about 10 mg per day per kg body weight of the recipient.

The efficacy of the peptides of the invention can be determined in vitro using the cell based assay described in Example 5 below.

Following methodologies which are well-established in the art, effective doses and toxicity of the compounds and compositions of the instant invention, which performed well in in vitro tests, are then determined in studies using small animal models (e.g., mice, rats or dogs) in which have been found to be therapeutically effective and in which these drugs can be administered by the same route proposed for the human trials.

For any pharmaceutical composition used in the methods of the invention, the therapeutically effective dose can be estimated initially from animal models to achieve a circulating plasma concentration range that includes the $IC_{50}$ (i.e., the concentration of the test compound which achieves a half-maximal inhibition of tumor mass). Dose-response curves derived from animal systems may be used to determine testing doses for administration to humans. In safety determinations for each composition, the dose and frequency of administration should meet or exceed those anticipated for use in any clinical trial.

As disclosed herein, the dose of the components in the compositions of the present invention is determined to ensure that the dose administered continuously or intermittently will not exceed an amount determined after consideration of the results in test animals and the individual conditions of a patient. A specific dose naturally varies (and is ultimately decided according to the judgment of the practitioner and each patient's circumstances) depending on the dosage procedure, the conditions of a patient or a subject animal such as age, body weight, sex, sensitivity, feed, dosage period, drugs used in combination, seriousness of the disease, etc.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$. Compositions that exhibit large therapeutic indices are preferred.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition. Cold Spring Harbor, N.Y.: Cold Spring Harbor Laboratory Press, 1989 (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); Ausubel, F. M. et al. (eds.). *Current Protocols in Molecular Biology*. John Wiley & Sons, Inc., 1994.

The present invention is also directed to isolated nucleic acids (DNA and RNA) encoding the peptides of the present invention), biologically active fragments of the peptides and analogs thereof and sequence conservative variants thereof. "Sequence conservative variants" of nucleic acid sequences are those in which a change of one or more nucleotide in a given codon position results in no alterations in the amino acid encoded at that position.

The peptides of the invention may be prepared by classical methods known in the art. These standard methods include exclusive solid phase synthesis, partial solid phase synthesis methods, fragment condensation, classical solution synthesis, and recombinant DNA technology [See, e.g., Merrifield J. Am. Chem. Soc. 1963 85:2149].

A preferred method for peptide synthesis is solid phase synthesis. Solid phase peptide synthesis procedures are well-known in the art [see, e.g., Stewart *Solid Peptide Syntheses* (Freeman and Co.: San Francisco) 1969; 2002/2003 General Catalog from Novabiochem Corp, San Diego, USA; Goodman *Synthesis of Peptides and Peptidomimetics* (Houben-Weyl, Stuttgart) 2002]. There are two main protocols used for the solid phase synthesis of proteins. The first uses the tertiary-butyloxycarbonyl (BOC) group as a protecting group and the second uses 9-fluorenylmethyloxycarbonyl (FMOC) as a protecting group (reviewed in Borgia, J. A. and Fields, G. B., [BTECH, 18:243-251 2000].

These solid phase synthesis methods can also be used to synthesize peptides in which amino acids other than the 20 naturally occurring, genetically encoded amino acids are substituted at one, two, or more positions of any of the compounds of the invention. Synthetic amino acids that can be substituted into the peptides of the present invention include, but are not limited to, N-methyl, L-hydroxypropyl, L-3,4-dihydroxyphenylalanyl, δ amino acids such as L-δ-hydroxylysyl and D-δ-methylalanyl, L-α-methylalanyl, β amino acids, and isoquinolyl. D-amino acids and non-naturally occurring synthetic amino acids can also be incorporated into the peptides of the present invention.

In addition, the peptides of the present invention can be produced recombinantly using appropriate microbial, yeast, insect or mammalian expression systems well known by those of ordinary skill in the art, using nucleic acids encoding the peptides.

The formulations for use in the present invention include those suitable for oral, rectal, ophthalmic (including intravitreal or intracameral), nasal, topical (including buccal and sublingual), intrauterine, or parenteral (including subcutaneous, intraperitoneal, intramuscular, intravenous, intradermal, intracranial, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

It should be realized that the pharmaceutical formulations of the present invention need not contain therapeutically effective amounts of the peptides of the present invention as such effective amount can be obtained by administration of a plurality of such formulations.

The present invention is described below in working examples which are intended to further describe the invention without limiting the scope thereof.

EXAMPLES

Example 1

Peptide Isolation

Hamster melanoma cells (ATCC CRL 49, American Type Culture Collection, ATCC, Manassas, Va.) were seeded at a concentration of $1 \times 10^6$ in DMEM (Meditech #10-013) containing glucose, glutamine, pyruvate, and pen/strep (Bio Whittaker, Cat. No. 17-602E) with 10% fetal bovine serum (FBS) in Primaria flasks (Falcon) at 37° C. with 5% $CO_2$. Cells were re-fed every 2-3 days and grown to confluence. In order to avoid potential contamination with serum proteins, cells were weaned off serum by slowly reducing the serum concentration in the medium. The serum concentration reductions were performed by stepping down the amount of serum in the medium or weaning the serum concentration. The reduction schedule was: 10%, 5%, 1%, 0.5%, 0.2%, 0.1% and 0% (Serum Free, SF). The weaning was done at room temperature and the changes made every day. [The cells can be left at any of these concentrations for a few days or over the weekend.]

After the first change to SF, the medium was discarded and replaced with fresh SF. The cells were incubated for 3-4 days at 37° C. and the medium was collected. This is the starting material for the purification. The cells were re-fed with the above-described medium containing 5% FBS and maintained at 37° C. The cells were grown until confluent, the weaning process repeated and the final SF media pooled.

Example 2

Purification of the Peptide of the Present Invention

The material isolated in Example 1 above ("Conditional Media") was flash evaporated, lyophilized to dryness and reconstituted to its original volume with distilled $H_2O$. The peptide was purified using HPLC as described below.

An MCX cartridge (Waters OASIS MCO, 35 ml 6 gram LP Extraction Cartridge, Part #186000778) was used. All eluting solutions were HPLC grade and were made up to contain 0.1% trifluoroacetate (TFA). A vacuum pump was used to pull the solutions through the cartridge. The cartridge was equilibrated with 40 ml PBS without TFA. The cartridge was not allowed to dry during the procedure. The entire volume of the reconstituted media was passed through the cartridge (this is the non-binding fraction) and was discarded. The cartridge was washed with 35 ml $H_2O$/0.1% TFA (this was the "$H_2O$ fraction" and was discarded). The column was eluted with 35 ml Acetonitrite/TFA. This was saved as "$ACN_1$" and was yellow in color due to the presence of acidified phenol red from the media. The cartridge was then eluted with 35 ml propanol with 0.1% TFA and collected. This is the "$prop_1$" fraction. The column was then washed with tetrahydrofuran (THF) containing 0.1% TFA. This was the "THF" fraction and was discarded. The cartridge was then eluted with 35 ml propanol with 0.1% TFA and collected. This was the "$prop_2$" fraction. The cartridge was eluted with 35 mls ACN/TFA and collected. This was the "$ACN_2$" fraction. The two prop fractions were pooled and the two ACN fractions were pooled and lyophilized. Table 1 below shows the HPLC gradient used.

TABLE 1

HPLC Gradient

| Step | Time (mins) | Flow (ml/min) | Water | Acetonitrile | Propanol | THF | Curve |
|---|---|---|---|---|---|---|---|
| 1 | 0.01 | 11 | 100 | 0 | 0 | 0 | 6 |
| 2 | 7 | 11 | 100 | 0 | 0 | 0 | 6 |
| 3 | 12 | 11 | 0 | 100 | 0 | 0 | 1 |
| 4 | 24 | 11 | 0 | 100 | 0 | 0 | 6 |
| 5 | 36 | 11 | 0 | 0 | 100 | 0 | 6 |
| 6 | 41 | 11 | 0 | 0 | 100 | 0 | 6 |
| 7 | 48 | 11 | 0 | 0 | 0 | 100 | 6 |
| 8 | 55 | 11 | 0 | 0 | 0 | 100 | 6 |
| 9 | 64 | 11 | 0 | 0 | 100 | 0 | 6 |
| 10 | 73 | 11 | 0 | 0 | 100 | 0 | 6 |
| 11 | 80 | 11 | 0 | 100 | 0 | 0 | 6 |
| 12 | 83 | 11 | 0 | 100 | 0 | 0 | 6 |
| 13 | 90 | 11 | 100 | 0 | 0 | 0 | 11 |
| 14 | 119 | 11 | 100 | 0 | 0 | 0 | 6 |
| 15 | 119.1 | 1 | 100 | 0 | 0 | 0 | 6 |

The prop fractions were lyophilized and electrophoresed in a 10-20% polyacrylamide gradient gel (Bio. Rad., Catalog #161-1180) and stained with SYPRO (Molecular Probes). Nine hundred and fifty microliters of Laemmli sample buffer (obtained from Bio-Rad) into which 50 µl of B-mercaptoethanol was added was used as a sample buffer. Twenty microliters of sample buffer was added to the dry (lyophilized) sample and heated to 95° C. for 5 minutes. Fifteen microliters were then loaded on the gel which was run at 120 volts for 1 hour. Molecular weight standards (Kaleidoscope Polypeptide Standards, Bio.-Rad) were also run in an adjacent lane. The running buffer was Tris Tricine (Bio-Rad Catalog #161-0744).

The stained band was cut out from the gel and analyzed in a mass spectrometer as described below. A photograph of the stained gel is shown in FIG. 9.

Example 3

Amino Acid Sequence

The amino acid sequence of the peptide isolated from the pooled propanol fractions after electrophoresis described above was determined. The analysis required the use of a Kratos Axima MALDI-TOF Mass Spectrometer (MS) and an Applied Bio Systems MALDI-CID-MS/MS instrument due to the hydrophobicity of the peptide and the non-ionizable nature of the peptide by ESI. The methods used are described below.

Methods:

The propanol, acetonitrile (ACN) and tetrahydrofuran (THF) fractions described above were initially concentrated and desalted using Millipore C-18 Zip-Tips to remove sample contaminants and eluted with 70% ACN for electrospray or 80% ACN/0.1% TFA in 2 mg/mL AHCA for MALDI analysis. The propanol, THF and acetonitrile fractions were evaluated using the Kratos Axima CFR MALDI-TOF and Thermo LCQ Deca XP plus ion trap using electrospray ionization. Initial evaluation of the two ionization methods showed an inability of the sample to ionize by electrospray. The MALDI analysis yielded spectra showing two predominant ions at 1428.9 and 1098.8 amu in the propanol fraction with no ions seen in the acetonitrile or THF fractions. No sequence data was obtainable on the Axima instrument. An aliquot of the propanol fraction was C-18 Zip-Tipped to remove contaminants and eluted using 70% n-propanol/AHCA matrix onto an MALDI target plate and evaluated on the Applied Biosystems Qstar XL using the oMALDI source. This instrument allows for true CID MS/MS fragmentation and evaluation of the peptide sequence. The 1098 ion was evaluated using on the Qstar using Analyst QS for ion analysis and peptide sequencing.

Figure 5:
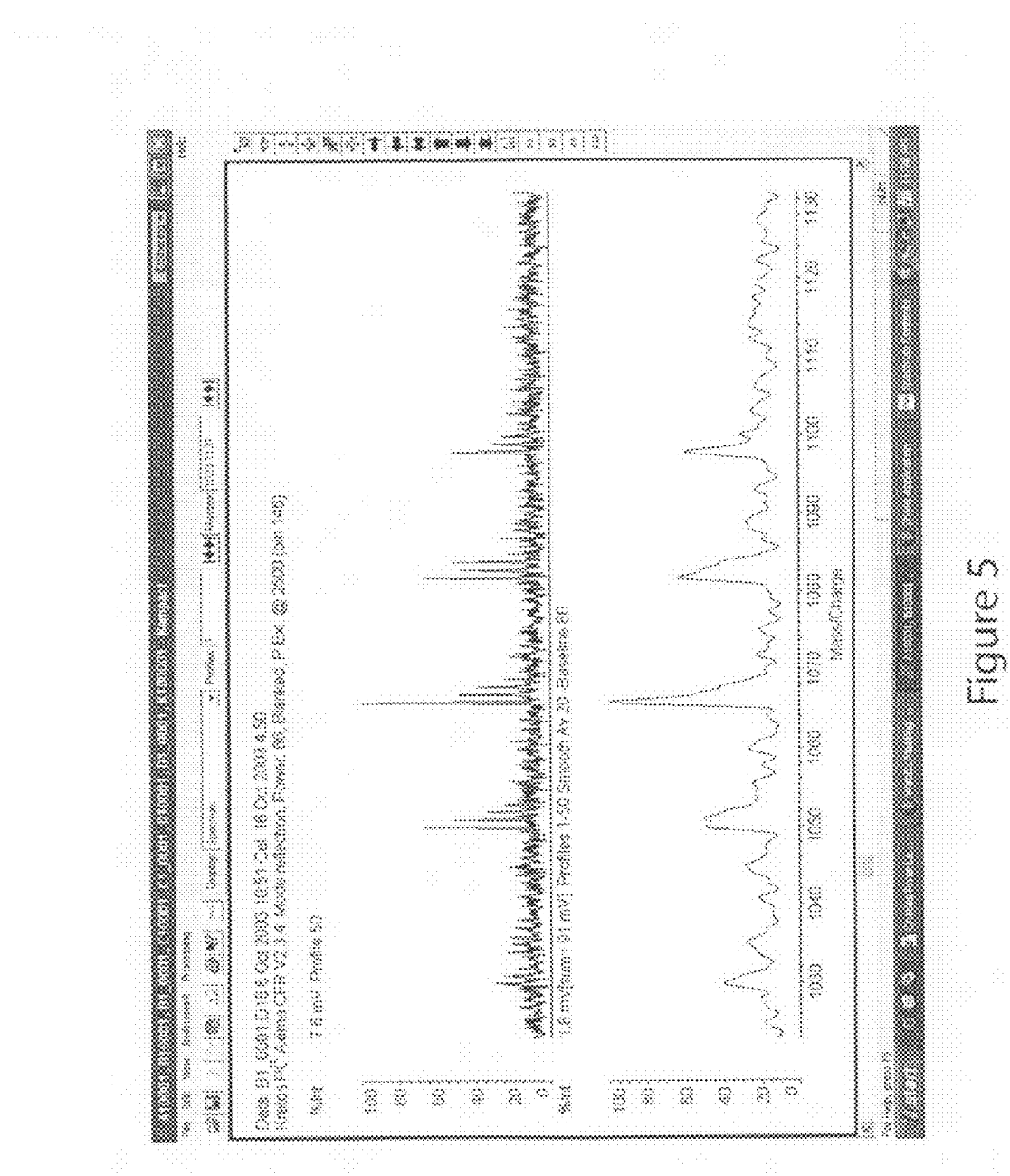
FIG. 5 is a graph showing the AXIMA MALDI-TOF MS of the Oxidized Methionine Series.
Figure 6:
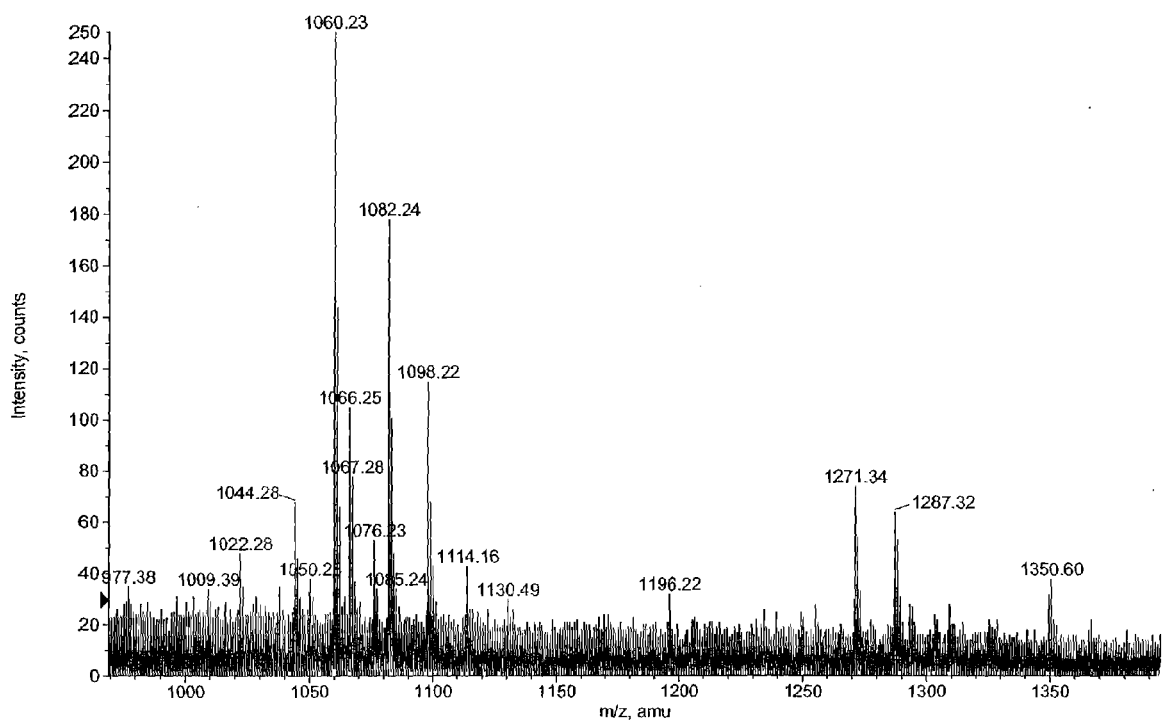
FIG. 6 is a graph showing the QSTAR MALDI-TOF-MS Spectra of the Propanol Fraction.
Figure 7:
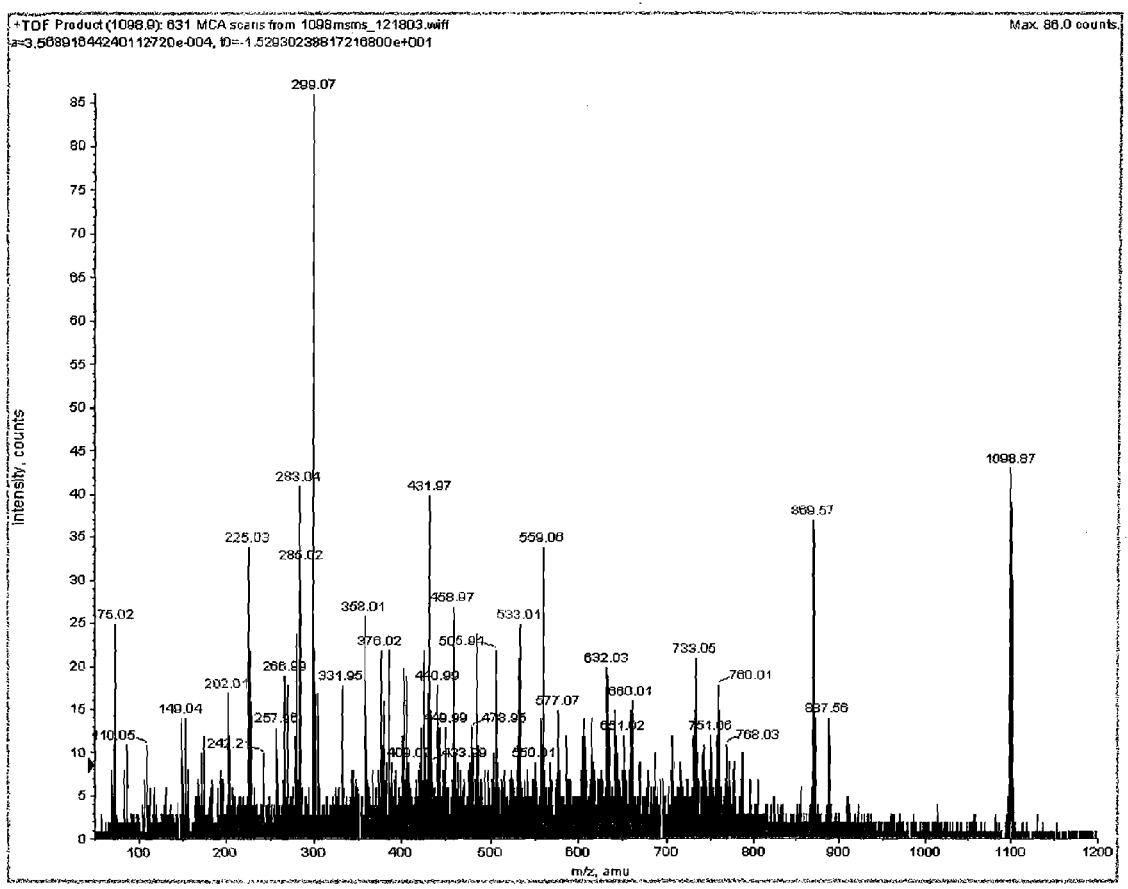
FIG. 7 is a graph showing the QSTAR MALDI-TOF MS/MS Spectra of the 1098 Ion.

Results/Discussion:

The three samples were evaluated on the Kratos MALDI-TOF MS instrument and the data can be seen in FIGS. 1-5. The propanol fraction yielded two strong ions at 1428.9 and 1098.8 with no other ions seen in the acetonitrile or THF fractions. Evaluation of the 1098.8 ion from the propanol fraction showed a series of ions at 1066, 1082 along with the 1098. The 16 amu difference is due to the oxidation of methionine where 16 mass units is from the addition of oxygen. This series is seen in FIG. 5. The propanol fraction was further analyzed using the Qstar XL instrument using the MALDI source. The TOF-MS spectra clearly show the 1066, 1082 and 1098 methionine oxidation series along with 1060 as the main ions in the spectra. The TOF-MS spectra can be seen in FIG. 6. MS/MS of the 1098 ion was performed generating a peptide fragment ion pattern seen in FIG. 7. Deconvolution of the fragmentation ions was performed using Analyst QS software allowing for the identification of the amino acid sequence. The MS/MS fragmentation of peptides at the alpha carbon of each amino acid usually occurs following specific patterns. This pattern is seen as y/b series or a/x series depending upon the alpha carbon bond broken. One series orientation is one n-terminus to c-terminus (b-ions) and one c-terminus to n-terminus (y-ions). This sequence is seen in the annotated sequence seen in FIG. 8 of the 1098 MS/MS spectra. One drawback of MALDI analysis is the production of ions in +1 charge state where peptide fragmentation is never as complete as seen with electrospray. This is because greater collision energy needs to be applied to the peptide to fragment leading to lower number of larger ions being generated and an abundance of lower molecular weight fragments. This effect is observed in the 890-1098 amu region and seen in FIG. 8.

Example 4

The following is the protocol followed to synthesize the two following cyclic peptides of the present invention.
326573   c(Gly-Met(O)-Met(O)-Cys-Val-Thr-His-Cys-Asn-Gly) [SEQ ID NO: 5]
324822   c(Gly-Met-Met-Cys-Val-Thr-His-Cys-Asn-Gly) w/Cys-Cys bridge [SEQ ID NO:6]
326573 Resin: 2.4 g of Fmoc-Val-PEG Resin (sub.: 0.21 mmol/g).

Peptide Synthesis: The peptide was synthesized by Fmoc-chemistry starting with Val. Coupling condition: 3.3 equiv. of Fmoc-AA-OH and 3.3 equiv. of HBTU, HOBt and NMM. The coupling was monitored by Ninhydrin Test.

Cleavage: The cleavage was done by Reagent K, 2.5 hr at RT. Yield 710 mg linear unprotected crude peptide.

Oxidation: 200 mg crude peptide was dissolved in 150 ml DMF and the pH was adjusted to ~8 by DIPEA. The oxidation was completed after three days (monitored by MS).

Cyclization: The oxidized peptide solution was added to 50 ml DMF (containing 520 mg PyBop, 136 mg HOBt and 350 ul DIPEA) dropwise. The mixture was stirred at room temperature for overnight and then concentrated to ~5 ml after completion (checked by MS).

The peptide was isolated by passing through RP-HPLC column (from Waters Corp.); the purity of the peptide was 99% on the profile.

Peptide 324822 was not the precursor of peptide 326573. It was synthesized separately.

For 324822, protected linear peptide was cleaved from resin and cyclized in DMF following the above procedure. After removing the protecting groups, the peptide was isolated by RP-HPLC purification.

Both peptides were not soluble in 100% aqueous solution. 10% acetonitrile in water was used to dissolve the peptides.

For 326573, was methionine sulfoxide synthesis using Fmoc-Met(O)—OH (methionine sulfoxide). Both Met are with sulfoxides. The peptide was started by mass analysis.

The following is a key to the terms in the above protocol:
HBTU—a coupling agent. 1-H-Benzotriazolium, 1-[Bis(dimethylamino)methelene]-hexa fluorophosphate (1-), 3-oxide.
NMM—another coupling agent. N-methylmorpholine.
DMF—dimethyl formamide
DIPEA—N,N-diisopropylethylamine
PyBop—a peptide coupling agent. Benzotriazol-1-yl-oxytripyrrolidinophosphonium hexafluorophosphate.
RP-HPLC—reverse phase HPLC
HOBt—1-hydroxybenzotriazole hydrate Example 5

Bioassay

Mouse melanoma cells—$B_{16}F_{10}$—were seeded in a 96 well plate at a concentration of 27,500 cells/well, in standard culture medium (DMEM). They were allowed to attach and spread for a period of about 4 hours, at which time the culture medium was replaced with (1) DMEM for the negative controls, (2) a sample of CIF with known, strong activity for the positive control and (3) the sample to be assayed for activity in the test wells. The wells are refed with the same media at 48 hours. They were scored for biological activity at 24, 48, 72 and 96 hours on a scale of 0 to 4. The assay is described in U.S. Pat. No. 4,307,062 and in greater detail below.

Materials and Methods

1. DMEM: 4.5 g/l glucose+glutamine, no pyruvate antibiotics (Pen/Strep) were added 10% fetal bovine serum (FBS)
2. Trypsin/EDTA Sigma T4174 (10×), Diluted to 1× with PBS
3. Cell line for assay: Mouse Melanoma: B16-F10: ATCC-CRL-6475
4. 25 cm² flasks
5. Positive Control—Sample of CIF previously known to be strongly positive.
6. Negative Control is 10% FBS DMEM
7. 96 well plate Method:
A. Trypsinization of Confluent Flask of B16-F10 Cells
  1. The medium was poured off
  2. The cells were rinsed with PBS
  3. 3 ml Trypsin/EDTA was added and incubated for ~1 min @37°
  4. The cells were shaken gently to detach cells
  5. 3 mls 10% FBS DMEM was added
  6. The solution was pipetted into a test tube and centrifuged at 2000 rpm/5 min
  7. The supernatant was decanted and cells resuspended in 5-10 ml 10% FBS DMEM
  8. The viability of cells was determined using Trypan Blue exclusion
B. The Cells were Counted and Diluted to Make 27,500 Viable Cells/0.2 ml
C. The Test Samples+Positive Control were Heat Inactivated
  1. 3.6 ml of each was incubated for 10 min×80° C.
  2. Cooled to room temperature
  3. 0.4 ml of FBS was added to each sample and Positive and Negative Controls. This is the 1:1 dilution
  4. 10% FBS DMEM was used to make higher dilutions. For the sample being assayed, 1:1, 1:2 and 1:4 dilutions are made.
96 well plate
  1. 0.2 ml distilled $H_2O$ was placed into the outer rim of wells to minimize evaporation.
  2. 0.2 ml of cells were placed into the wells. Cells were still in 10% FBS DMEM. Two wells for each dilution were used. A felt tip pen was used on the cover to identify samples in wells.

3. Incubated at 37° C. for 4 hours to allow cells to attach and spread.
4. The medium was removed and replaced with 0.2 mls of test media for the samples and the positive and negative controls.

E. Scoring
1. Results were evaluated at 24 and 48 hours. (If necessary, cells may be refed after 48 hours and scored again at 72 and 96 hours.)
2. Scoring scheme is from 0-4. It is a subjective interpretation, which will become more accurate with repetition. If possible, two observers note the scores independently and compare their readings.
   a. 0=no morphological change and no inhibition of growth. The samples are compared to Negative Control.
   b. 4+=All cells in well are elongated (fibroblast-like). They will be aligned like a school of fish. They are compared to the Positive Control.
   c. 3+=less elongation, less alignment
   d. 2+=some elongated, some elliptical, a few unaffected
   e. 1+=few elongated, many elliptical, some unaffected Example 6

Synthesis and Cyclization of a Peptide of the Present Invention

The peptide was synthesized by using the solid phase peptide synthesis (SPPS) method with Fmoc protection and cyclized. This peptide contains the fewest modifications—it does not have oxygenated methionine amino acid residue or disulfide bonds.

The peptide was synthesized according to the sequence starting from the C-terminus by using a resin containing the Gly residue. The side chain protections for the peptide during the synthesis were: Gly-Met-Met-Cys(Trt)-Val-Thr(tBu)-His(Trt)-Cys(Trt)-Asn(Trt)-Gly-resin [SEQ ID NO: 7]

The peptide, after synthesis, was cleaved from the resin with 1% TFA/DCM.

The side-chain protected peptide was head-to-tail cyclized with HATU/HOAT/DIEA/DMF.

The cyclized peptide was side chain-deprotected with TFA/$H_2O$.

The deprotected peptide was purified by reverse-phase HPLC.

The deprotected peptide was biologically active.

Example 4 contains the description for the reagents.

Example 7

The sample was prepared as in Examples 1 and 2 above and the sequence determined as in Example 3. The spectrogram is shown in FIG. 11. The same amino acid sequence as described above was found.

Example 8

One hundred fifty ml of conditioned medium from 10, 75 $mm^2$ flasks ($1 \times 10^8$ AM cells) was applied to a 6 gm, 35 ml MCX cartridge, set up and run as described in Example 2 above. 35 ml fractions were collected. 2 Acn fractions and 2 prop fractions (a total of 70 ml) were collected, lyophilized to dryness, redissolved in 2 ml of 0.1% TFA in water and applied to a 71 ml preparative $C_{18}$ HPLC column. The yield was 400 µg (the analytic yield was 40 µg).

Figure 12:
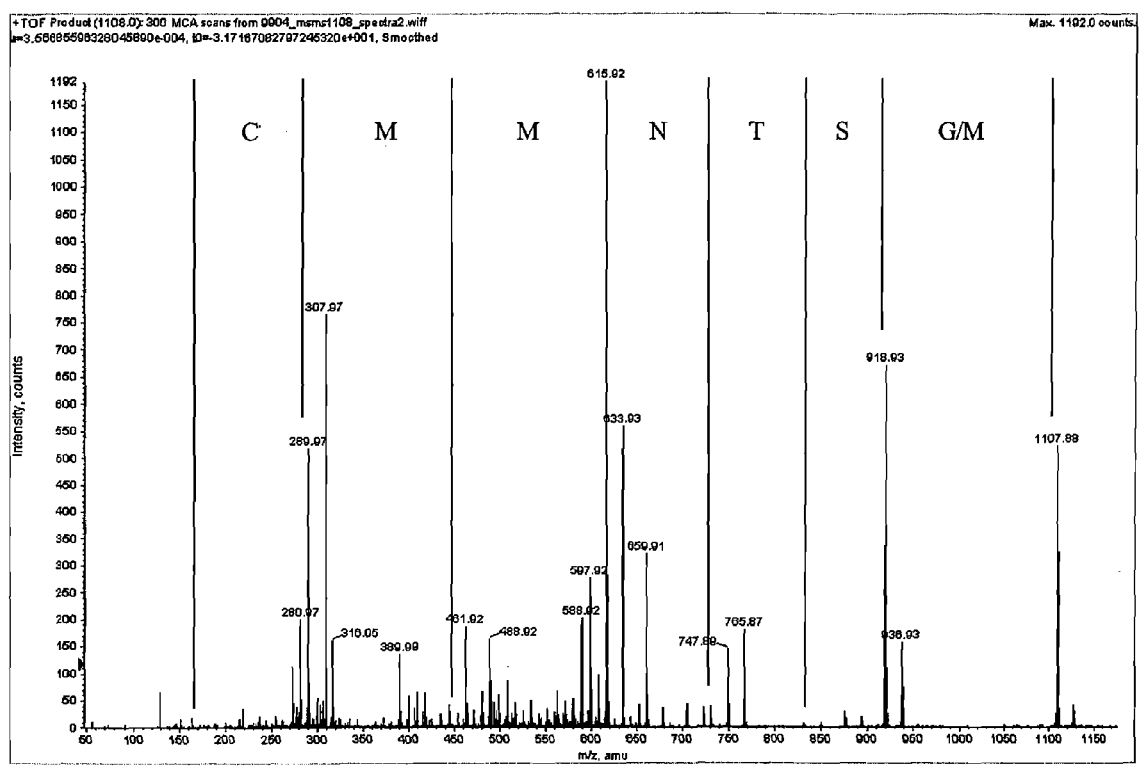
FIG. 12 is a mass spectrogram of the peptide of the present invention isolated from the conditioned media of amelanotic melanoma cells in culture and purified on a scaled-up preparative MCX column.

The mass spectrogram of the eluted material is shown in FIG. 12.

One potential amino acid sequence is Gly-Met-Cys-Val-Ser-His-Cys-Asn-Gly (SEQ ID NO 2). In addition, the methionines are oxygenated. It differs from the sequence in Example 3 above by a substitution of serine for threonine. As defined above, it is an analog.

Another potential amino acid sequence is Cys-Met-Met-Asn-Thr-Ser-Cys-Met-Val-Leu (SEQ ID NO:3).

Yet another potential amino acid sequence is Cys-Met-Met-Asn-Thr-Ser-Cys-Met-Val-Ile (SEQ ID NO:4). It is an analog of SEQ ID NO:3.

Paper Example 1

Assay for In Vivo Antitumor Activity

Twenty-four week old hamsters (Bar Harbor Labs, Bar Harbor, N.H.) will be implanted subcutaneously with 40,000 cells of a malignant melanoma cell line (AM cells, RPMI 1846, American Type Culture Collection). There will be 2 groups, one control and one experimental; 10 animals per group. Treatment will begin on day 6. The experimental group will receive 0.2 µg/kg body weight of the peptide described in Example 6 above in 1 ml of 0.1M PBS, pH 7.2. The control group will receive 1 ml of PBS. The injections will be administered intraperitoneally on a daily schedule for 30 days.

The dimensions of the tumor will be measured using calipers as described in George Lipkin et al., "Can Modulation of the Malignant Phenotype by an Endogenous Inhibitor Lead to Tumor Regression In Vivo?", in The Pharmacological Effect of Lipids, Vol. 3, J. Kabara (Ed.), Amer. Oil. Chem. Soc., Champaign, Ill. (1990). The volume of the tumor will be calculated using the formula volume=[width×height×length]×½

REFERENCES

Barnhill et al., *Lab Investig.* 67:331-337 (1992).

Folkman, J., New York: Academic Press 43:175-203 (1985).

Graham et al., *Am J Pathol* 145:510-514 (1994).

Norris et al., *J Invest Dermatol*, 90:783, 789 (1988).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. An isolated nucleic acid encoding the peptide as set forth in SEQ ID NO: 1.

2. An isolated nucleic acid encoding the peptide as set forth in SEQ ID NO: 2.

3. An isolated nucleic acid encoding the peptide as set forth in SEQ ID NO: 3.

4. An isolated nucleic acid encoding the peptide as set forth in SEQ ID NO: 4.

5. A purified, isolated peptide comprising the amino acid sequence as set forth in SEQ ID NO. 5.

6. A purified, isolated peptide comprising the amino acid sequence as set forth in SEQ ID NO. 6 wherein said peptide contain a disulfide bond between residues 4 (cys)and 8 (cys).

7. A purified, isolated peptide comprising the amino acid sequence as set forth in SEQ ID NO. 7.

* * * * *